(12) United States Patent
Drozdov et al.

(10) Patent No.: US 12,026,980 B2
(45) Date of Patent: Jul. 2, 2024

(54) PUPIL ELLIPSE-BASED, REAL-TIME IRIS LOCALIZATION

(71) Applicant: BLINK TECHNOLOGIES INC., Palo Alto, CA (US)

(72) Inventors: Gilad Drozdov, Haifa (IL); Nadav Arbel, Tel Aviv (IL); Tsahi Mizrahi, Yoqneam Ilit (IL); Soliman Nasser, Haifa (IL); Artyom Borzin, Haifa (IL); Uri Wollner, Ramat Gan (IL); Oren Haimovitch-Yogev, Los Altos, CA (US)

(73) Assignee: BLINK TECHNOLOGIES INC., Palo Alto, CA (US)

( * ) Notice: Subject to any disclaimer, the term of this patent is extended or adjusted under 35 U.S.C. 154(b) by 574 days.

(21) Appl. No.: 17/376,388

(22) Filed: Jul. 15, 2021

(65) Prior Publication Data

US 2022/0019791 A1  Jan. 20, 2022

Related U.S. Application Data

(60) Provisional application No. 63/052,480, filed on Jul. 16, 2020.

(51) Int. Cl.
| | | |
|---|---|---|
| *A61B 3/00* | (2006.01) | |
| *A61B 3/11* | (2006.01) | |
| *A61B 3/113* | (2006.01) | |
| *A61B 3/14* | (2006.01) | |
| *A61H 5/00* | (2006.01) | |
| *G02B 27/00* | (2006.01) | |
| *G02B 27/01* | (2006.01) | |
| *G06T 7/00* | (2017.01) | |
| *G06T 7/13* | (2017.01) | |
| *G06T 7/73* | (2017.01) | |
| *G06V 40/19* | (2022.01) | |
| *H04N 13/302* | (2018.01) | |
| *H04N 13/327* | (2018.01) | |
| *H04N 13/383* | (2018.01) | |

(52) U.S. Cl.
CPC ............ *G06V 40/19* (2022.01); *A61B 3/0025* (2013.01); *A61B 3/112* (2013.01); *G02B 27/0093* (2013.01); *G02B 27/017* (2013.01); *G06T 7/13* (2017.01); *G06T 2207/30041* (2013.01)

(58) Field of Classification Search
CPC ....... A61B 3/0091; A61B 3/022; A61B 3/032; A61B 3/14; G06T 7/0012; G06T 7/246; G06T 7/73; G06T 2207/30041; G06T 2207/30201; A61H 5/005; H04N 13/279; H04N 13/302; H04N 13/327; H04N 13/383
See application file for complete search history.

*Primary Examiner* — Jack Dinh
(74) *Attorney, Agent, or Firm* — AlphaPatent Associates Ltd.; Daniel J. Swirsky

(57) ABSTRACT

The disclosure relates to systems, methods and programs for developing real-time user-specific eye model based on iris localization using solely pupil-ellipse analysis.

20 Claims, 5 Drawing Sheets

PUPIL ELLIPSE-BASED, REAL-TIME IRIS LOCALIZATION

CROSS-REFERENCE TO RELATED APPLICATIONS

The present application claims the benefit of priority to U.S. Provisional Application No. 63/052,480, entitled PUPIL ELLIPSE-BASED, REAL-TIME IRIS LOCALIZATION, naming Uri Wollner, Nadav Arbel, Tsahi Mizrahi, Soliman Nasser, Artyom Borzin, Gilad Drozdov and Oren Haimovitch-Yogev as inventors, filed 16 Jul. 2020, the content of which is hereby incorporated by reference in its entirety.

COPYRIGHT NOTICE

A portion of the disclosure herein below contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND

The disclosure is directed to systems, methods and programs for use in gaze estimation, eye tracking, and/or calibration of head-mounted displays (HMD). More specifically, the disclosure is directed to systems, methods and programs for developing real-time user-specific eye model based on iris localization using solely pupil-ellipse analysis.

Eye tracking and gaze estimation can, and is used in a large area of applications from ophthalmology, disabled's assistive technologies, through advertising, cybersecurity authentication, to gaming and virtual reality. Precisely detecting the pupil's contour and the eyeball center is the first step in many of the tasks associated with these applications, hence the need to perform the detection and information analysis accurately. Typically, camera-based eye tracking approaches are normally divided into two stages: eye/pupil detection and gaze estimation based on that information.

Likewise, gaze-estimation can be divided into two approaches; 2D appearance/feature-based and 3D model-based. Appearance/feature-based methods are typically based on the assumption that similar eye appearances/features (e.g., eye corners, elliptical tilt and dimensions), correspond to similar gaze positions/directions, from which different mapping functions can be learned to perform gaze estimation. Conversely, 3D model-based methods perform gaze estimation based on a 3D geometric eye model, which mimics the structure and function of human vision system.

However, the practical utility of both these methods (appearance/feature based and model-based) can be significantly limited due, for example, to complex system (e.g., IR illumination source, stereo vision system, 3D sensors setup and the like) and sensitivity to environmental settings such as light, distance and head pose. Moreover, using current technology, these methods may either; have strong limiting assumptions, are commercially unfeasible, or are insufficiently accurate.

These and other shortcomings of the existing technologies are sought to be resolved herein.

SUMMARY

Disclosed, in various embodiments, are systems, methods and programs for developing real-time user-specific eye model from a plurality of images, based on iris localization and using solely pupil-ellipse analysis.

In an embodiment provided herein is a computerized method of establishing a user-specific eye model, implementable in a system comprising a head-mounted imaging module (HMI) configured for an off-axis capture of the user's eyes, a central processing module in communication with an operator interface module, an edge detection module, a rendering module, and a display, the method comprising: using the HMI, capturing a plurality of images of the user's eye; for each image, estimating an eyeball center $E_C$, projecting eyeball to image plane, thereby identifying a major axis R of projected pupil ellipse; rendering a directional vector $\vec{p}$, emanating from pupil center being normal to the pupil's major axis R toward the eyeball center $E_C$, from pupil center in each image, rendering limbus visibility angle intersected by directional vector, forming limbus' probable visibility angles $\theta_1$, and $\theta_2$; using the edge detection module, applying edge detection to each image, forming a plurality of edge rendered images; in each edge rendered image, rendering a pair of rays inscribing limbus visibility angle $\theta_{PL}$: detecting the intersection point of each of the pair of rays with the second edge detected, thereby detecting limbus points $LP_1$, and $LP_2$ for each edge rendered image, and using the detected limbus points from all captured images; compiling the user-specific eye-model wherein a smaller circle intersects a larger circle in two intersection points corresponding to the user-specific limbus.

In another embodiment, provided herein is a processor-readable media implementable in a computerized system comprising a head-mounted imaging module (HMI) configured for an off-axis capture of the user's eyes, a central processing module in communication with an operator interface module, an edge detection module, a rendering module, and a display, the central processing module further comprising a non-volatile memory having thereon the processor readable media with a set of instructions configured, when executed to cause the central processing module to: using the HMI, capture a plurality of images of the user's eye, for each image, estimate an eyeball center $E_C$; project eyeball to image plane, and identify a major axis R of projected pupil ellipse; render a directional vector $\vec{p}$, emanating from pupil center being normal to the pupil's major axis R toward the eyeball center $E_C$, from pupil center in each image, render limbus visibility angle $\theta_{PL}$, intersected by directional vector, forming limbus' probable visibility angles $\theta_1$, and $\theta_2$; using the edge detection module, apply edge detection to each image, forming a plurality of edge rendered images, in each edge rendered image, render a pair of rays inscribing limbus visibility angle $\theta_{PL}$: detect the intersection point of each of the pair of rays with the second edge detected, thereby detecting limbus points $LP_1$, and $LP_2$ for each edge rendered image; and using the detected limbus points from all captured images; compile the user-specific eye-model wherein a smaller circle intersects a larger circle in two intersection points corresponding to the user-specific limbus.

These and other features of the systems, methods and programs for developing real-time user-specific eye model based on iris localization using solely pupil-ellipse analysis, will become apparent from the following detailed description when read in conjunction with the figures and examples, which are exemplary, not limiting.

BRIEF DESCRIPTION OF THE FIGURES

For a better understanding of systems, methods and programs for developing real-time user-specific eye model based on iris localization using solely pupil-ellipse analysis, with regard to the embodiments thereof, reference is made to the accompanying examples and figures, in which.

DETAILED DESCRIPTION

Provided herein are embodiments of systems, methods and programs for developing real-time user-specific eye model based on iris localization using solely pupil-ellipse analysis.

The provided systems, methods and programs are adapted, when implemented, to provide an estimate of the location the eyeball center and eyeball radius solely based on iris points localized in multiple images. Therefore, the user does not have to recalibrate the system every time the head-mounted display (HMD) moves, or if the user removes the HMD and then puts it back on.

The provided systems, methods and programs are adapted, when implemented, to provide an estimate of the location the eyeball center and eyeball radius solely based on iris points localized in multiple images. Therefore, the user does not have to recalibrate the system every time the head-mounted display (HMD) moves, or if the user removes the HMD and then puts it back on. The disclosed systems, methods and programs (processor-readable media e.g.) can be extremely beneficial for user experience in HMD-type setting. The continuous and automatic calibration of the user's eyeball center without the need for user's input is an advantage. Moreover, the disclosed and claimed technology is not only limited to HMD setting, but can also be altered to provide a solution for eyeball location other related applications, such as in webcam setting as well, where user attention and saliency analysis may be desired.

Included in the term "head-mounted display" (HMD) refers to visors, goggles and spectacles worn directly on the head, and also such articles carried indirectly on the head by being mounted on a helmet, or other head gear. It also comprises visors, goggles and viewing windows which are built into helmets or other head gear. Moreover, HMDs can also describe one or more of the following: a wearable computer having a display, head mounted electronic device, a head-coupled display, a head-mounted computer with a display. The HMD, which his worn on a head of a user or which is a part of a helmet, can have a small display optic in front of one (monocular display device) or each eye (binocular display device). Also, the HMD can have either one or two small displays with lenses and semi-transparent mirrors embedded in a helmet, eye-glasses (also known as data glasses) or visor. The display units can be miniaturized and may include a Liquid Crystal Display (LCD), Organic Light-Emitting Diode (OLED) display, or the like. Some vendors employ multiple micro-displays to increase total resolution and field of view. Some other HMDs do not use a traditional display at all and instead project light directly into the user's eyes. Also included in the HMD are contact lenses equipped with imaging and connectivity (brain, remote) capabilities.

Figure 1:
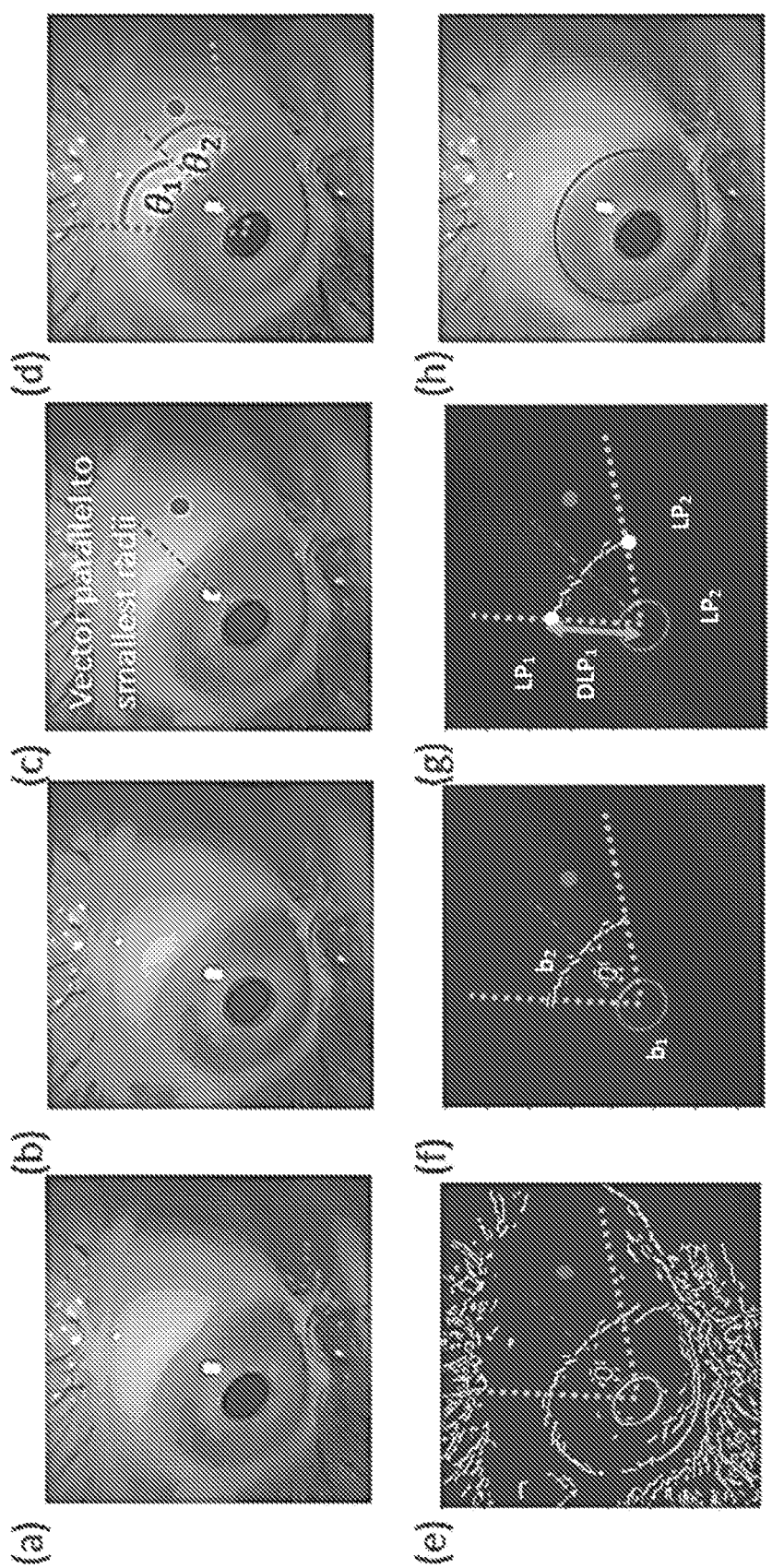
FIG. 1 shows the results of an embodiment of the method of extracting limbus points from a single image, where: (a) Initial image. (b) Pupil is located in the image. (c) A ray extending the axis corresponding to the smallest radii of the pupil ellipse (dashed) and projected estimated eyeball center (red dot). (d) Two angles are determined to cover a region of interest with respect to the ray determined in (c). (e) Canny edge filter is applied to original image (a). The edge map (e) is filtered using the region of interest found in (d). (g) The edges that have the highest bin count as a function of normalized distance from the center of the pupil are kept. (h) Estimation of the iris contour upon optimization of the 3D eye model.
Figure 2:
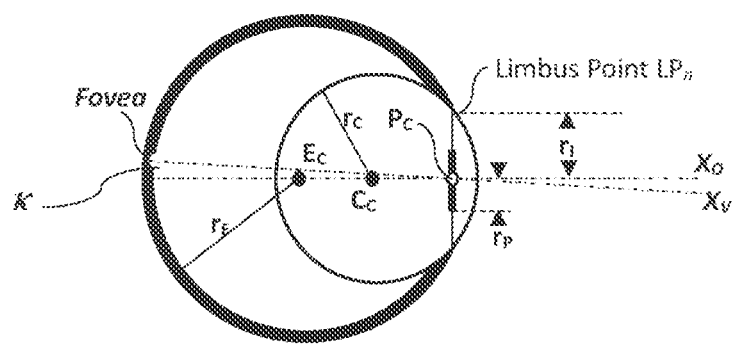
FIG. 2, is a schematic of an eye model.
Figure 3:
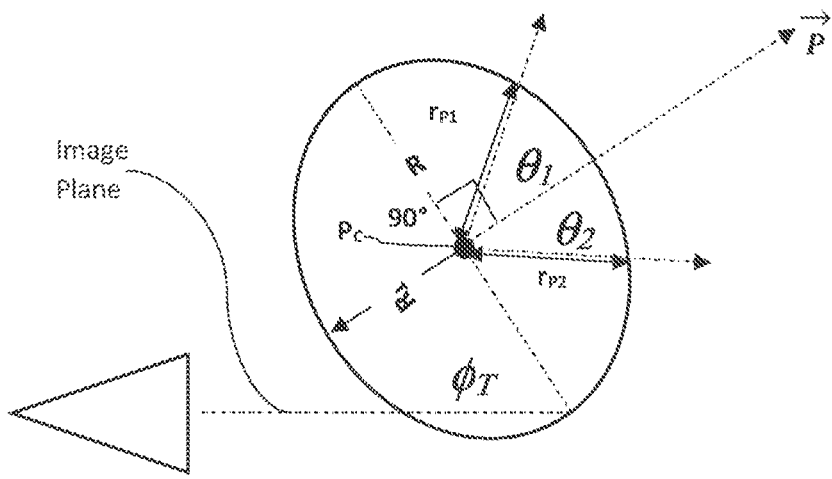
FIG. 3, is a schematic of the pupil ellipse.
Figure 4:
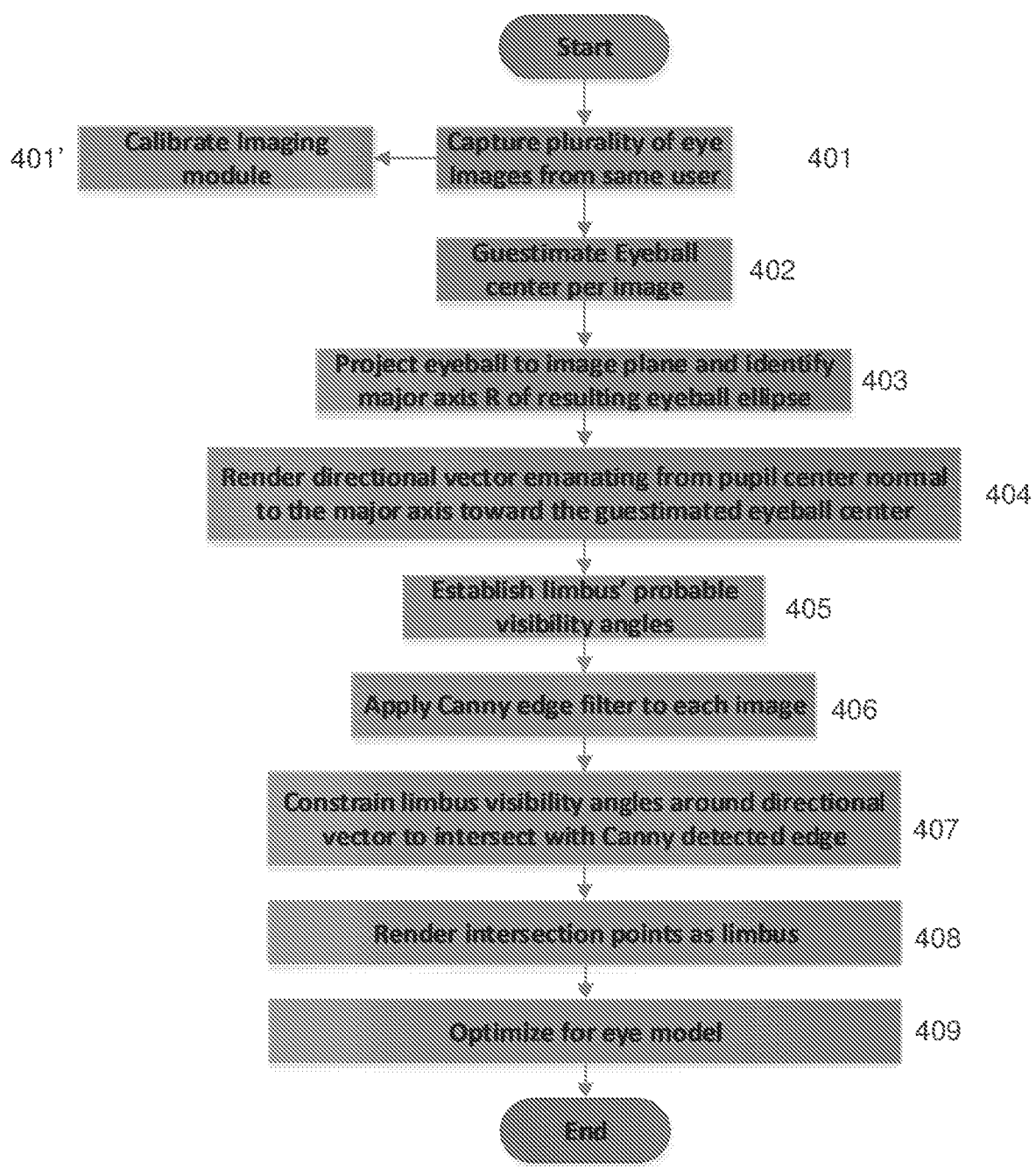
FIG. 4, is a flow chart of an embodiment of the methods.

Accordingly and in an embodiment illustrated in FIGS. 2-4), provided herein is a computerized method of establishing a user-specific eye model (see e.g., FIG. 2), implementable in a system comprising a head-mounted imaging module (HMI) configured for an off-axis, head-mounted capture of the user's eyes, a central processing module in communication with an operator interface module, an edge detection module, a rendering module, and a display, the method comprising, using the HMI, capturing a plurality of images of the user's eye 401; for each image, estimating an eyeball center $E_C$ 402 (see e.g., FIG. 2, $E_C$); projecting eyeball to image plane 403 (see e.g., FIG. 3), thereby identifying a major axis R (see e.g., FIG. 3) of projected pupil ellipse; rendering a directional vector $\vec{p}$ (see e.g., FIGS. 3, 1c), emanating from pupil center (see e.g., $P_C$, FIG. 3), being normal to the pupil's major axis R and parallel with the projected pupil ellipse's minor axis, toward the guestimated (in other words, based initially on incomplete information) eyeball center $E_C$ 404, after establishing visibility angle $\theta_{PL}$ 405, from pupil center ($P_C$, see e.g., FIG. 3), in each image, rendering limbus visibility angled $\theta_{PL}$ (see e.g., FIGS. 3, 1d) intersected by directional vector $\vec{p}$, forming limbus' probable visibility angles $\theta_1$, and $\theta_2$ (see e.g., FIGS. 3, 1d) Then, using the edge detection module 406, applying edge detection to each image, forming a plurality of edge rendered images (see e.g., FIG. 1e); in each edge rendered image, rendering a pair of rays 407 (see e.g., FIGS. 1f, 3) inscribing limbus visibility angle $\theta_{PL}$. The limbus visibility angle $\theta_{PL}$, can be between about 30° and about 90°, for example 60°, respectively making $\theta_1$, and $\theta_2$, each between about 15° and about 45°, for example 30°. Then detecting the intersection point of each of the pair of rays with the second edge detected 408 (see e.g., $b_2$—corresponding to the detected limbus, FIG. 1f), thereby detecting limbus points $LP_1$, and $LP_2$ (see e.g., FIG. 1g) for each edge rendered image; and using the detected limbus points $LP_n$ from all captured images; compiling the user-specific eye-model 409 wherein a smaller circle intersects a larger circle (see e.g., FIG. 2) in two intersection points corresponding to the user-specific limbus.

In the compilation of the user-specific eye model, the recorded limbus locations or points $LP_n$ of all captured images are used in an optimization scheme to construct a 3D eye model consisting of sphere and a circular contour lying on the surface of the sphere (SEE e.g., FIG. 2). That is, the circular feature correspond to that created on a plane intersecting the sphere. (FIG. 1h). The loss of the minimization function required for constructing the intersecting circles is dependent on the corneal projection error of the estimated iris in 3D and the error associated with the $LP_n$ found in the plurality of captured images. In other words, for the iris-based calibration the eyeball center is estimated based on multiple frames with localized limbus points ($LP_n$). The method thus yield four variables, x, y, z of eyeball center and iris-center eyeball-center offset, represented by the equation (1):

$$\hat{x}, \hat{y}, \hat{z}, \overline{offset} = \operatorname{argmin}_{x,y,z,offset} \sum_{i=1}^{N} \left| \sum_{j=1}^{M} dist(LP_{i,j} - \wp(R_i(EM))) \right|_2$$

Where, EM is the eye model, $\mathcal{R}$ (EM) is the rotation matrix applied to the eye model, and $\wp(\cdot)$ is the projection of the 3D iris onto the image plane.

Furthermore, identifying the major axis R (see e.g., FIG. 3) of projected pupil ellipse in each initially captured image, can further comprise detecting pupil ellipse in each image; recording the detected pupil's ellipse's major axis length and unproject each ellipse to a circle in three-dimensional (3D) space, then combine unprojected circles (in other words, a circle which when projected to the image plane (see e.g., FIG. 3), would yield the ellipse identified), from each of the plurality of captured images, thereby forming a 3D pupil motion model and refining the 3D pupil motion model for each originally captured image. Moreover, since the imaging module is head-mounted, the whole process and method takes place in the imaging module space, obviating the need for constraining the process by head pose, such that the gaze vector returned once calculated, is relative to the imaging module. Accordingly and in an embodiment, simultaneously with the capturing of the plurality of images, a calibration of the imaging module can be done to ascertain its intrinsic characteristics.

Figure 5:
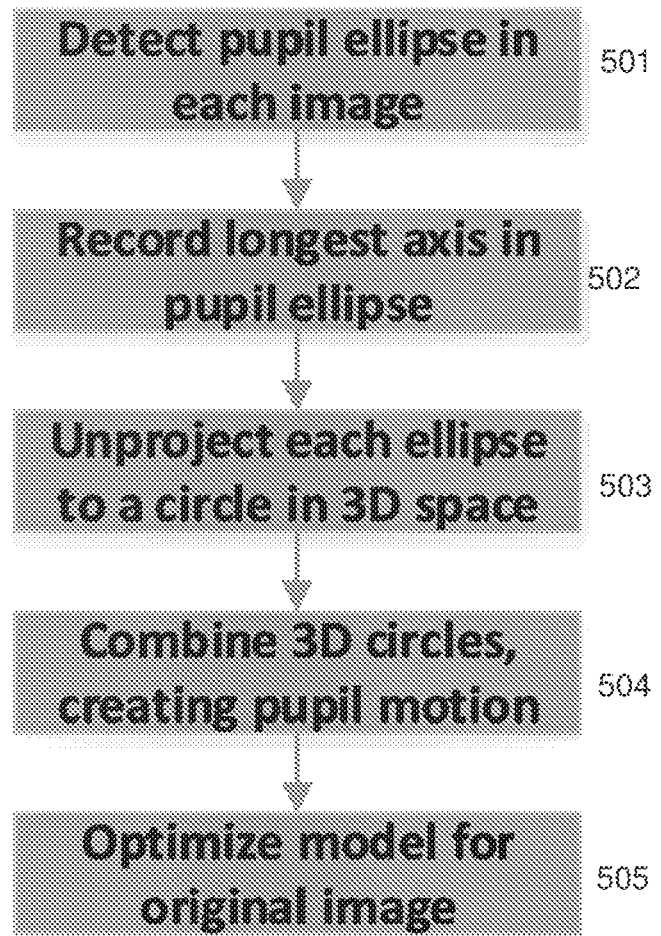
FIG. 5, is a flow chart for extracting pupil ellipse information.
Figure 6:
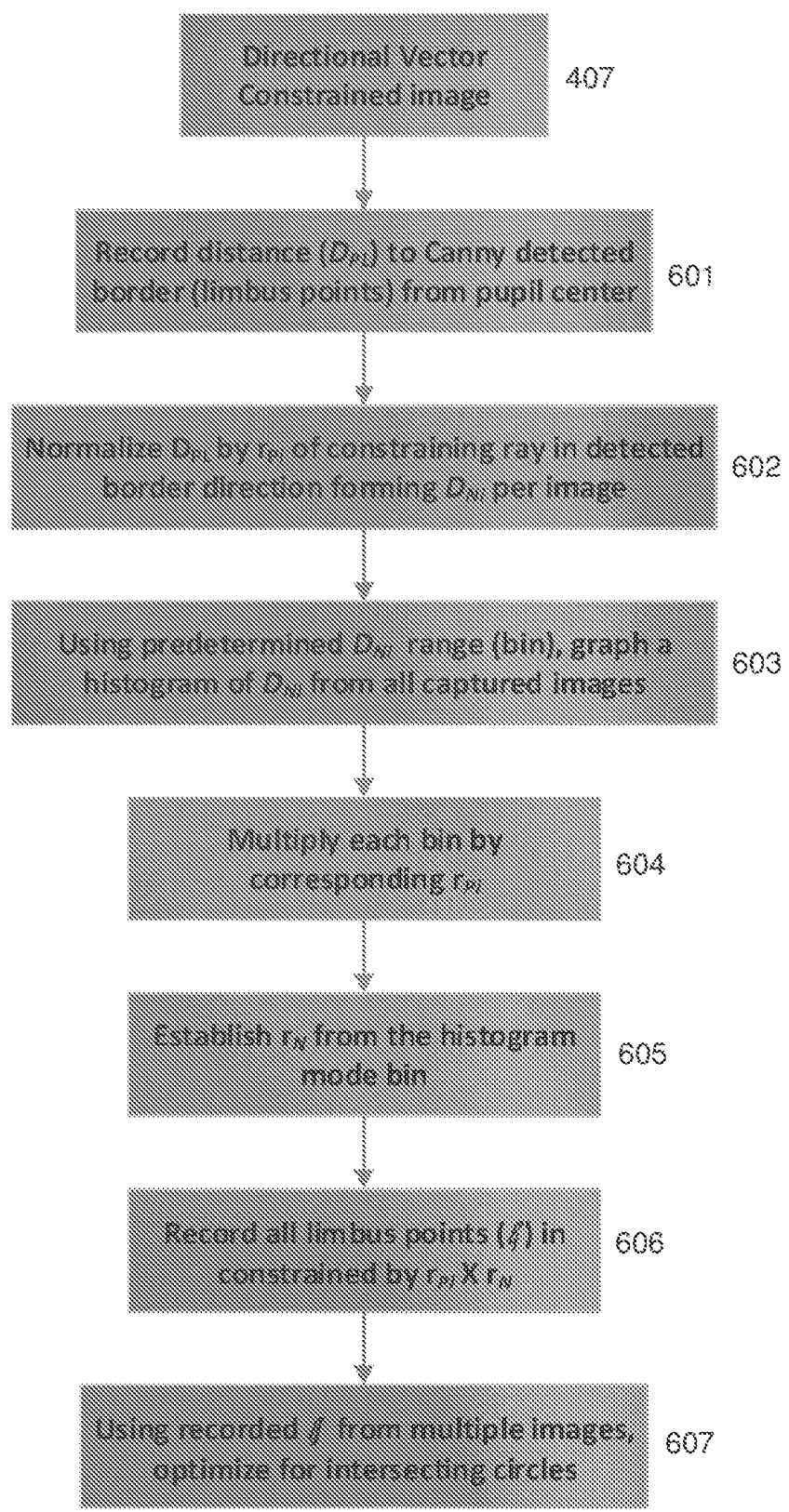
FIG. 6, is a flow chart for rendering the user's iris based on the pupil information.

As illustrated in FIG. 5, first the pupil ellipse in each image is independently detected 501. This is done by, for example, approximating the pupil region using a fast, simple feature detection (see sample algorithm below); followed by, for example, the use of a k-means histogram segmentation to refine the approximation of the pupil region. Additionally using the imaging module, an initial approximation to the pupil center $P_C$ is carried out and the length of the pupil's ellipse major axis R, its midpoint, the minor axis $R_\perp$, and the tilt angle $\phi_T$ (see e.g., FIG. 3) are measured and recorded 502. Finally, the pupil center $P_C$ is refined and its elliptical outline established, using, for example an ellipse fitting algorithm. Accordingly and in an embodiment, the step of applying edge detection to each image (see e.g., 406, FIG. 4), forming a plurality of edge rendered images, is preceded by a step of applying a Gaussian filter to each of the captured images in 401.

The following is an example of an algorithm that can be used to fit detected pupil ellipse:

```
procedure RANSAC-ELLIPSE-FIT(points, image, N, ε)
    best-ellipse ← null
    best-support ← - inf
    // Perform N RANSAC iterations
    repeat N times
        sample ← RANDOM-SAMPLE(points, 5)
        ellipse ← FIT-ELLIPSE(sample)
        // Early sample rejection
        If ∃(x, y) ∈ sample where
            Vellipse(x, y) · Vimage(x, y) ≤ 0 then
            continue // reject sample, skip this iteration
        end if
        // Iteratively refine inliers (we use M = 2)
        repeat M times
            inliers = {(x, y) ∈ points | error(ellipse, x, y) < ε}
            ellipse ← FIT-ELLIPSE(inliers)
        end repent
        // Calculate the support of the ellipse
        support ← support(ellipse, image, inliers)
        If support > best-support then
            best-ellipse ← ellipse
            best-support ← support
        end if
        // Early termination for ≥ 95% inliers
        If |inliers| ≥ 0.95 · |points| then
            break
        end if
    end repeat
    return best-ellipse
end procedure
```

Finding the pupil center can be done, for example whereby for each eye image, using the imaging module, the unprojected pupil circle $(p_i;n_i;r_i)$ is established, where i is the index of the individual initially captured image (the $i^{th}$ image), with the aim to find a single sphere which is tangent to every $i^{th}$ pupil circle. Since each pupil circle is tangent to the sphere, the normals of the $i^{th}$ circles, $n_i$, will be radial vectors of the sphere, and thus their intersection can be considered as the unifying sphere's and thus the pupil's center. Other methods for finding the ellipse boundaries and center can be used with the methods provided herein. These can be, for example at least one of: using a monocular image module that zooms in on only one eye of the user, capture the images and discern a single unprojected circle, and where pupil center is computed based solely on points related to the pupil boundary computing a curvature value for each detected boundary point.

Returning now to FIGS. 1g, and 3, the methods and programs implemented in the systems disclosed and claimed herein further comprise measuring a radius of the pupil along each of the pair of rays $r_{Pi}$ (see e.g., FIG. 3), inscribing limbus visibility angle $\theta_{PL}$, establishing ray-specific radii $r_{P1}, r_{P2}$, for each individually captured image (or in the case of video capturing, each isolated frame along a time line axis).

In an embodiment, the step of applying edge detection to each image, forming a plurality of edge rendered images, comprises using a Canny edge detector 406, referring to a method that is widely used in computer vision to locate sharp intensity changes and to find object boundaries in an image. The Canny edge detector classifies a pixel as an edge once it is determined that the gradient magnitude of the pixel is larger than those of pixels at both its sides in the direction of maximum intensity change Consequently, since edges are marked at maxima in gradient magnitude, a Gaussian-smoothed image is produced by applying a Gaussian filter, having, for example, a kernel of no less than 5 pixels by 5 pixels.

A typical Canny edge detection can be:
a. In order to optimize the trade-off between noise filtering and edge localization an appropriate Gaussian filter is applied to reduce desired image details;
b. Determine gradient magnitude and gradient direction at each pixel, using for example, approximations of partial derivatives;
c. If the gradient magnitude at a pixel is larger than those at its two neighbors in the gradient direction, mark the pixel as an edge. Otherwise, mark the pixel as the background. In other words, the edges are sharpened by applying non-maxima suppression to the gradient magnitude; and
d. Remove the weak edges by (double) hysteresis thresholding. In thresholding, all values below threshold (T) value are changed to 0, which means that selecting a proper values for T can be challenging, since some false edges may remain if T is too low, while some edges will disappear if T is too high and some edges may disappear due to softening of the edge contrast by shadows or occlusion.

Turning now to FIGS. 1*e-h*, 3, 4 and 6 the steps of detecting limbus points $LP_1$, and $LP_2$ for each edge rendered image 408 and compiling the user-specific eye-model 409 comprise, for each rendered ray inscribing limbus visibility angle $\theta_{PL}$ (see e.g., FIGS. 1*e*, 3), recording distance $D_{PLq}$ from the pupil center to second detected edge 601 in each edge detected image thereby identifying $D_{LP1}$, and $D_{LP2}$ (see e.g., FIG. 1*g*), for each edge rendered image; normalizing each of $D_{LP1}$, and $D_{LP2}$, by the respective $r_{P1}$, $r_{P2}$ 602 (see e.g., FIG. 3), thereby identifying normalized distances $D_{N1}$ and $D_{N2}$ for each edge rendered image; using a predetermined normalized distance range to establish a plurality of bins 603, building a histogram of $D_{LP1}$, and $D_{LP2}$ from all captured images; multiplying 604 each bin content by its corresponding $r_{Pi}$; selecting 605 the normalizing radius $r_N$ from the histogram mode bin (in other words, the bin with the largest count of $D_{N1}$, $D_{N2}$); rendering limbus points ($l_j$) detected from all the captured images 606 constrained by $r_{Pi} \times r_N$; and using all detected $l_j$, from all captured images (see e.g., FIG. 1*g*), optimizing 607 for a model of intersecting circles, wherein a plane formed by the intersection of the smaller circle and the bigger circle is defined by the contour of the detected $l_j$. The number of images is configured such that the variance of the pupil location with respect to the projected eyeball center is large enough. In an embodiment, the number of images is no less than 9, for example, between 9 and 90.

It is noted that the term "imaging module" as used herein means a head mounted device unit that includes a plurality of built-in image and/or optic sensors and outputs electrical signals, which have been obtained through photoelectric conversion, as an image, while the term "module" refers to software, hardware, for example, a processor, or a combination thereof that is programmed with instructions for carrying an algorithm or method. The modules described herein may communicate through a wired connection, for example, a hard-wired connections, a local area network, or the modules may communicate wirelessly. The imaging module may comprise charge coupled devices (CCDs), a complimentary metal-oxide semiconductor (CMOS) or a combination comprising one or more of the foregoing. If static images are required, the imaging module can comprise a digital frame camera, where the field of view (FOV) can be predetermined by, for example, the camera size and the distance from the subject's face. The cameras used in the imaging modules of the systems and methods disclosed, can be a digital camera. The term "digital camera" refers in an embodiment to a digital still camera, a digital video recorder that can capture a still image of an object and the like. The digital camera can comprise an image capturing unit or module, a capture controlling module, a processing unit (which can be the same or separate from the central processing module).

Capturing the image can be done with, for example image capturing means such as a CCD solid image capturing device of the full-frame transfer type, and/or a CMOS-type solid image capturing device, or their combination. Furthermore and in another embodiment, imaging module can have a single optical (e.g., passive) sensor having known distortion and intrinsic properties, obtained for example, through a process of calibration. These distortion and intrinsic properties are, for example, modulation-transfer function (MTF), focal-length for both axes, pixel-size and pixel fill factor (fraction of the optic sensor's pixel area that collects light that can be converted to current), lens distortion (e.g., pincushion distortion, barrel distortion), sensor distortion (e.g., pixel-to-pixel on the chip), anisotropic modulation transfer functions, space-variant impulse response(s) due to discrete sensor elements and insufficient optical low-pass filtering, horizontal line jitter and scaling factors due to mismatch of sensor-shift- and analog-to-digital-conversion-clock (e.g., digitizer sampling), noise, and their combination. In an embodiment, determining these distortion and intrinsic properties is used to establish an accurate sensor model, which can be used for calibration algorithm to be implemented.

To facilitate some operations of the methods and programs described, the system can further comprise a graphic processing module (GPM), in communication with the central processing module and the processor. It should be understood though, that the graphics processing module may or may not be a separate integrated circuit.

The systems used herein is a computerized systems; further comprising a central processing module; a display module, and a user interface module. The Display modules, which can include display elements, which may include any type of element which acts as a display. A typical example is a Liquid Crystal Display (LCD). LCD for example, includes a transparent electrode plate arranged on each side of a liquid crystal. There are however, many other forms of displays, for example OLED displays and Bi-stable displays. New display technologies are also being developed constantly. Therefore, the term display should be interpreted widely and should not be associated with a single display technology. Also, the display module may be mounted on a printed circuit board (PCB) of an electronic device, arranged within a protective housing and the display module is protected from damage by a glass or plastic plate arranged over the display element and attached to the housing.

Additionally, "user interface module" broadly refers to any visual, graphical, tactile, audible, sensory, or other means of providing information to and/or receiving information from a user or other entity. For example, a set of instructions which enable presenting a graphical user interface (GUI) on a display module to a user for displaying and changing and or inputting data associated with a data object in data fields. In an embodiment, the user interface module is capable of displaying any data that it reads from the imaging module.

As indicated, the systems implementing the methods provided, using the programs provided can further comprise a central processing module; a display module; an edge detection module, and a user interface module. The term 'module', as used herein, means, but is not limited to, a software or hardware component, such as a Field Programmable Gate-Array (FPGA) or Application-Specific Integrated Circuit (ASIC), which performs certain tasks. A module may advantageously be configured to reside on an addressable storage medium and configured to execute on one or more processors. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules.

Unless specifically stated otherwise, as apparent from the discussions, it is appreciated that throughout the specification discussions utilizing terms such as "processing," "loading," "in communication," "detecting," "calculating," "determining", "analyzing," or the like, refer to the action and/or processes of a computer or computing system, or similar electronic computing device, that manipulate and/or transform data represented as physical, such as the PoR into other data similarly represented as physical layers, such as the transformed data.

As indicated, provided herein is a computer program, comprising program code means for carrying out the steps of the methods described herein, as well as a computer program product (e.g., a micro-controller) comprising program code means stored on a medium that can be read by a computer, such as a hard disk, CD-ROM, DVD, USB memory stick, or a storage medium that can be accessed via a data network, such as the Internet or Intranet, when the computer program product is loaded in the main memory of a computer [or micro-controller] and is carried out by the computer [or micro controller].

Furthermore, provided herein is a computer-readable medium comprising the executable instructions disclosed. Accordingly, provided herein is processor-readable media implementable in the computerized systems described herein, whereby the central processing module further comprising a non-volatile memory having thereon the processor readable media with a set of instructions configured, when executed to cause the central processing module to: using the HMI, capture a plurality of images of the user's eye; for each image, estimate an eyeball center $E_C$; project eyeball to image plane, and identify a major axis R of projected pupil ellipse; render a directional vector $\vec{p}$, emanating from pupil center being normal to the pupil's major axis R toward the eyeball center $E_C$; from pupil center in each image, render limbus visibility angle $\theta_{PL}$, intersected by directional vector, forming limbus' probable visibility angles $\theta_1$, and $\theta_2$; using the edge detection module, apply edge detection to each image, forming a plurality of edge rendered images; in each edge rendered image, render a pair of rays inscribing limbus visibility angle $\theta_{PL}$: detect the intersection point of each of the pair of rays with the second edge detected, thereby detecting limbus points $LP_1$, and $LP_2$ for each edge rendered image, and using the detected limbus points from all captured images; compile the user-specific eye-model wherein a smaller circle intersects a larger circle in two intersection points corresponding to the user-specific limbus.

The term "computer-readable medium" as used herein, in addition to having its ordinary meaning, refers to any medium that participates in providing instructions to a processor for execution. Such a medium may take many forms, including but not limited to, non-volatile media and volatile media. Non-volatile media can be, for example, optical or magnetic disks, such as a storage device. Volatile media includes dynamic memory, such as main memory.

Memory device as used in the methods, programs and systems described herein can be any of various types of memory devices or storage devices. The term "memory device" is intended to encompass an installation medium, e.g., a CD-ROM, floppy disks, or tape device; a computer system memory or random access memory such as DRAM, DDR RAM, SRAM, EDO RAM, Rambus RAM, etc.; or a non-volatile memory such as a magnetic media, e.g., a hard drive, optical storage, or ROM, EPROM, FLASH, etc. The memory device may comprise other types of memory as well, or combinations thereof. In addition, the memory medium may be located in a first computer in which the programs are executed (e.g., a training computer), and/or may be located in a second different computer [or micro controller] which connects to the first computer over a network, such as the Internet and might be even not connected and information will be transferred using USB drive. In the latter instance, the second computer may further provide program instructions to the first computer for execution.

The term "memory device" can also include two or more memory devices which may reside in different locations, e.g., in different computers that are connected over a network.

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the stack(s) includes one or more stack). Reference throughout the specification to "one embodiment", "another embodiment", "an embodiment", and so forth, when present, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

Although the foregoing disclosure for systems, methods and programs for developing real-time user-specific eye model based on iris localization using solely pupil-ellipse analysis has been described in terms of some embodiments, other embodiments will be apparent to those of ordinary skill in the art from the disclosure herein. Moreover, the described embodiments have been presented by way of example only, and are not intended to limit the scope of the embodiments. Indeed, the novel methods, programs, and systems described herein may be embodied in a variety of other forms without departing from the spirit thereof. Accordingly, other combinations, omissions, substitutions and modifications will be apparent to the skilled artisan in view of the disclosure herein.

While the invention has been described in detail and with reference to specific embodiments thereof, it will be apparent to one of ordinary skill in the art that various changes and modifications can be made therein without departing from the spirit and scope thereof. Accordingly, it is intended that the present disclosure covers the modifications and variations of this invention provided they come within the scope of the appended claims and their equivalents.

What is claimed:

1. A computerized method of establishing a user-specific eye model, implementable in a system comprising a head-mounted display (HMD) configured for an off-axis capture of at least one image of at least one eye of a user, the method comprising:
   a. using the HMD, capturing a plurality of images of at least one of the user's eyes;
   b. for each image, estimating an eyeball center $E_C$ of an eyeball;

c. projecting the eyeball to an image plane, thereby identifying a major axis R of a projected pupil ellipse;
d. calculating a directional vector $$\vec{p},$$

emanating from a pupil center, being normal to the major axis R, and being directed towards from the eyeball center $E_C$;
e. from the pupil center in each image, calculating limbus visibility angle $\theta_{PL}$, intersected by directional vector $$\vec{p},$$

forming limbus probable visibility angles $\theta_1$, and $\theta_2$;
f. applying edge detection to each image, forming a plurality of edge-rendered images;
g. in each edge-rendered image, calculating a pair of rays inscribing limbus visibility angle $\theta_{PL}$;
h. detecting the intersection point of each of the pair of rays with a second detected edge, thereby detecting limbus points $LP_1$, and $LP_2$ for each edge-rendered image; and
i. using the detected limbus points from a plurality of captured images, compiling the user-specific eye-model.

2. The method of claim 1, wherein the step of identifying the major axis R of the projected pupil ellipse comprises:
a. detecting a pupil ellipse in each image;
b. determining the detected ellipse's major axis length;
c. unprojecting each pupil ellipse to a circle in three-dimensional (3D) space; and
d. combining unprojected circles from each image, thereby forming a 3D pupil motion model.

3. The method of claim 2, further comprising measuring a radius of the pupil along each of the pair of rays $r_{Pi}$, inscribing limbus visibility angle $\theta_{PL}$, establishing ray-specific radii $r_{P1}$, $r_{P2}$, for each image.

4. The method of claim 3, wherein the pupil center is established as the mid-point of the detected major axis R of the pupil ellipse.

5. The method of claim 4, wherein the steps of detecting limbus points $LP_1$, and $LP_2$ for each edge-rendered image and compiling the user-specific eye-model comprise:
a. for each ray inscribing limbus visibility angle $\theta_{PL}$, recording distance $D_{PLq}$ from the pupil center to the second detected edge in each edge-detected image thereby identifying $D_{PL1}$, and $D_{PL2}$, for each edge-rendered image;
b. normalizing each of $D_{PL1}$ and $D_{PL2}$, by the respective $r_{P1}$ and $r_{P2}$, thereby identifying normalized distances $D_{N1}$ and $D_{N2}$ for each edge-rendered image;
c. using a predetermined normalized distance range to establish a plurality of bins to build a histogram of $D_{PL1}$ and $D_{PL2}$ from one or more captured images;
d. multiplying each bin content by its corresponding $r_{Pi}$;
e. selecting the normalizing radius $r_N$ from the histogram mode bin,
f. calculating limbus points $(l_j)$ detected from one or more of the captured images constrained by $r_{Pi} \times r_N$; and
g. using the detected limbus points $(l_j)$ to optimize a model of intersecting circles, wherein a plane formed by an intersection of a smaller ellipse representing the pupil with a larger ellipse representing the iris is defined by the contour of the detected limbus points $(l_j)$.

6. The method of claim 1, wherein the step of applying edge detection to each image, forming a plurality of edge-rendered images comprises using a Canny edge detector.

7. The method of claim 6 further comprising, for each projected pupil ellipse, measuring at least one of pupil center location, pupil radii, or pupil tilt angle.

8. The method of claim 7, further comprising recalculating the eyeball center $E_C$.

9. The method of claim 1, wherein the step of applying edge detection to each image, forming a plurality of edge-rendered images, is preceded by a step of applying a Gaussian filter to each of the captured images.

10. The method of claim 9, wherein the Gaussian filter indicates movement of the HMD relative to the eyeball.

11. A processor-readable medium implementable in a computerized system having a head-mounted display (HMD) configured for an off-axis capture of at least one image of at least one eye of a user, the processor-readable medium having a set of instructions configured, when executed, to cause the computerized system to:
a. using the HMD, capture a plurality of images of at least one of the user's eyes;
b. for each image, estimate an eyeball center $E_C$ of an eyeball;
c. project the eyeball to an image plane, and identify a major axis R of a projected pupil ellipse;
d. calculate a directional vector $$\vec{p},$$

emanating from a projected pupil center, being normal to the major axis R, and being directed away from the eyeball center $E_C$;
e. from the pupil center in each image, calculate limbus visibility angle $\theta_{PL}$, intersected by directional vector $$\vec{p},$$

forming limbus' probable visibility angles $\theta_1$, and $\theta_2$;
f. apply edge detection to each image, forming a plurality of edge-rendered images;
g. in each edge-rendered image, calculate a pair of rays inscribing limbus visibility angle $\theta_{PL}$;
h. detect the intersection point of each of the pair of rays with a second detected edge, thereby detecting limbus points $LP_1$, and $LP_2$ for each edge-rendered image; and
i. using the detected limbus points from the plurality of captured images, compile the user-specific eye-model.

12. The processor-readable medium of claim 11, wherein, in identifying the major axis R, the set of instructions is further configured when executed to:
a. detect a pupil ellipse in each image;
b. measure the detected ellipse's major axis length;
c. unproject each pupil ellipse to a circle in three-dimensional (3D) space; and
d. combine unprojected circles from each image, thereby forming a 3D pupil motion model.

13. The processor-readable medium of claim 12, wherein the set of instructions is further configured when executed to: measure a radius of the pupil along each of the pair of rays $r_{Pi}$, inscribing limbus visibility angle $\theta_{PL}$, establishing ray-specific radii $r_{P1}$, $r_{P2}$, for each image.

14. The processor-readable medium of claim 13, wherein the pupil center $P_C$ is established as the mid-point of the detected major axis R of the pupil ellipse.

15. The processor-readable media of claim 14, wherein, to detect limbus points $LP_1$, and $LP_2$ for each edge-rendered image and compile the user-specific eye-model, the set of instructions is further configured when executed to:
   a. for each ray inscribing limbus visibility angle $\theta_{PL}$, record distance $D_{PLq}$ from the pupil center to the second detected edge in each edge-detected image thereby identifying $D_{PL1}$, and $D_{PL2}$, for each edge-rendered image,
   b. normalize each of $D_{PL1}$ and $D_{PL2}$ by the respective $r_{P1}$ and $r_{P2}$, thereby identifying normalized distances $D_{N1}$ and $D_{N2}$ for each edge-rendered image;
   c. using a predetermined normalized distance range to establish a plurality of bins, build a histogram of $D_{PL1}$ and $D_{PL2}$ from one or more captured images;
   d. multiply each bin content by its corresponding $r_{Pi}$;
   e. select the normalizing radius $r_N$ from the histogram mode bin;
   f. calculate limbus points ($l_j$) detected from one or more of the captured images constrained by $r_{Pi} \times r_N$; and
   g. using the detected limbus points ($l_j$), optimize a model of intersecting circles, whereby a plane formed by an intersection of a smaller circle representing the pupil and a larger circle representing the iris is defined by a contour corresponding to the detected limbus points ($l_j$).

16. The processor-readable medium of claim 15, wherein the set of instructions is further configured when executed to recalculate the eyeball center $E_C$ based on an optimized user-specific eye-model.

17. The processor-readable medium of claim 11, wherein the set of instructions to apply edge detection to each image, forming a plurality of edge-rendered images is configured when executed to apply a Canny edge detector.

18. The processor-readable medium of claim 17, wherein the set of instructions is further configured when executed to measure at least one of pupil center location, pupil radii, or pupil tilt angle.

19. The processor-readable medium of claim 11, wherein, the set of instructions to apply edge detection to each image, forming a plurality of edge-rendered images is further configured when executed to: first apply a Gaussian filter to each of the captured images.

20. The processor-readable medium of claim 19, wherein the Gaussian filter indicates movement of the HMD relative to the eyeball.

* * * * *